Dec. 3, 1935. F. H. HOWARD Plant Pat. 158
ROSE
Filed July 23, 1935
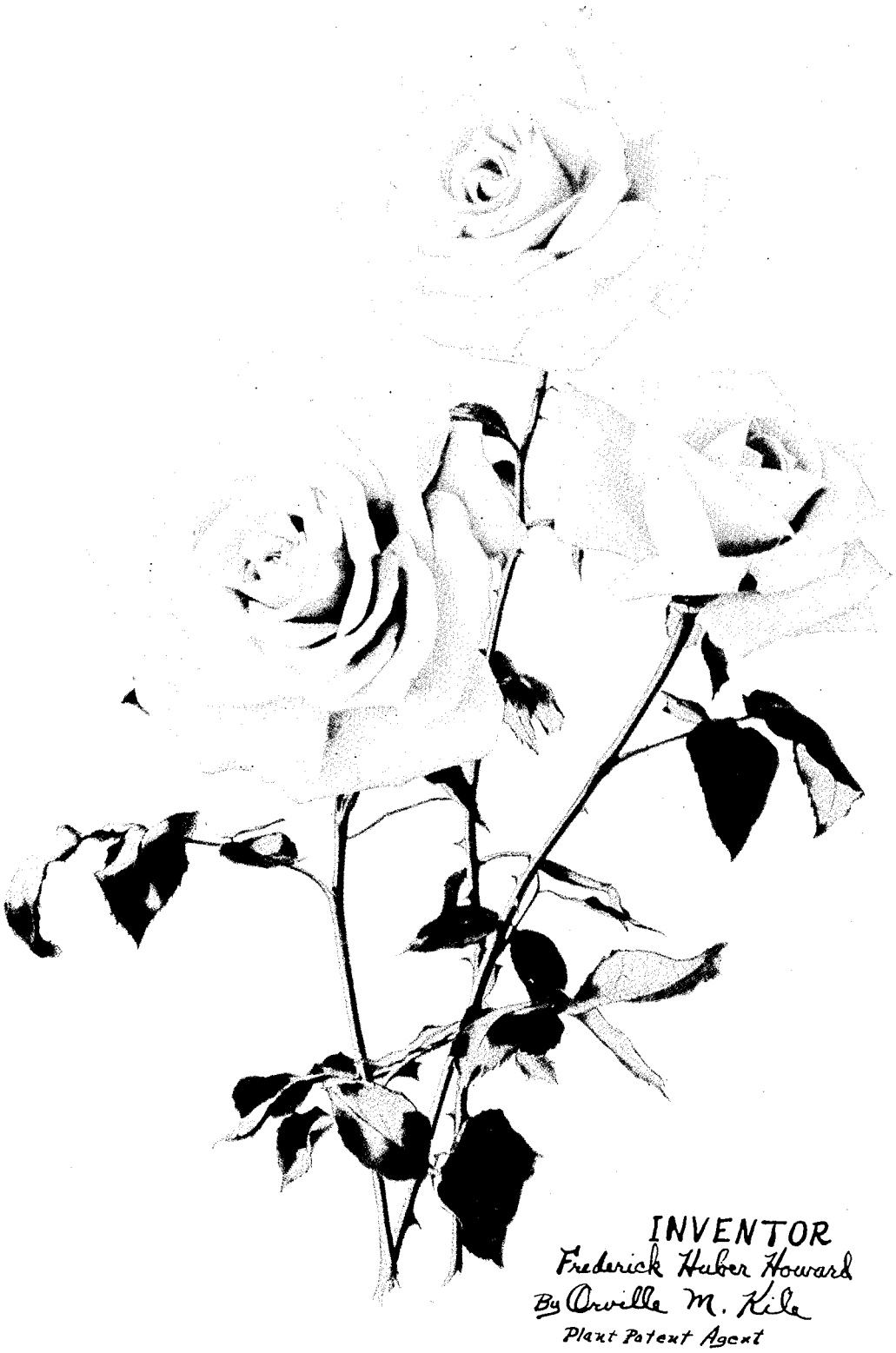
INVENTOR
Frederick Huber Howard
By Orville M. Kile
Plant Patent Agent Patented Dec. 3, 1935

Plant Pat. 158

UNITED STATES PATENT OFFICE

158

ROSE

Frederick Huber Howard, Montebello, Calif., assignor to Henry A. Dreer, Incorporated, Philadelphia, Pa., a corporation of New Jersey Application July 23, 1935, Serial No. 32,807

1 Claim. (Cl. 47—61)

My present invention concerns improvements in fragrant hybrid tea roses of a red color. This new rose is the result of careful plant breeding work carried on by myself and my associates in California, and is a cross between the two varieties Premier Supreme and Lady Leslie.

The accompanying illustration shows in full natural colors, blossoms in various stages of maturity, also some of the stems and foliage—all depicted as nearly as possible in their true forms and colors, and based on observations on flowers grown in southern California (except where otherwise noted).

The following is a more detailed description of this rose plant and its flowers:

*The bush or plant.*—Very large in size, being a very strong grower and under favorable conditions reaching a height of five or six feet in a single season. It is a very heavy producer of flowers, giving at least one-third greater production than the related variety Mrs. J. D. Eisele, also originated by myself. Its profuse foliage and large size make it a desirable bedding variety.

When plants are cut back to three eyes in greenhouse work, they break freely and show no blind shoots. Each shoot produces a single bud at the tip, rarely more.

This new variety, in California, is resistant to both black-spot and mildew.

*Stems.*—Inclined to be thin rather than stout, but amply able to bear the blossoms upright; slightly zig-zag rather than straight; light elm green in color (Plate XVII, Ridgway's Color Standards and Nomenclature); beset with a few small straight pinkish thorns, pointing slightly downward.

*Leaves.*—Compound, of 5 to 7 leaflets each, small and comparatively narrow and pointed as compared with their length, usually about 1¾ inches long by 1½ inches wide; approximately elm green in color (Plate XVII, Ridgway's Color Standard and Nomenclature). The leaves are generally reflexed from the stem; have moderately serrated edges and rather deep-set midribs. An occasional leaflet is so deeply notched as to give the appearance of being split on one side. The underneath surfaces on the newer leaves have a pinkish cast. The rachis is of medium size and commonly bears one or two very small thorns or prickles on its nether side.

*Stipules.*—Quite small, narrow, and terminating in very small but sharp points.

*The flower*

Flowers are borne singly, on medium to long stems. When field grown, new canes often branch into three to five flower stems each bearing a single flower with a stem six to eight inches long after the manner of Red Radiance.

*Buds.*—Moderately long and pointed.

*Sepals.*—Relatively short, reaching merely to top of the bud. Each sepal has two small side branches and only an occasional sepal shows moderate foliaceous tendency. The calyx is a much lighter green than the stem or foliage.

*Blossoms.*—As the buds open the centers are revolute in form; the unfolding petals take a regular, even position, giving the whole flower a refined and "perfect" appearance. This perfection of form is retained throughout the life of the flower.

The flower is quite large in size, measuring 4¾ to 5 inches across the top when fully opened. It has 40 large to medium-sized petals and 10 to 12 small central petals during June in central New Jersey. It is rather flat in form but the outer rows of petals curl back extensively and produce a high center effect, but not a pointed high center.

The stamens are numerous, slightly pinkish in color and are mounted with yellow to terra-cotta colored anthers. The pistils are numerous, somewhat longer than the stamens, white for two-thirds of their length, then pink, and topped with white stigmas. Sterile except by artificial pollenization.

The color is popularly described as deep coral rose, very rich in quality, but the color shown in Ridgway's Color Standard and Nomenclature most nearly approaching that of this rose is called Rose Red (Plate XII). The flower is, however, somewhat lighter in color than Rose Red—in some lights approaching "Rose Color". Slight yellowish area at point of attachment.

The distribution of this color is quite even over the petals although somewhat darker on the inside surfaces than on the outside surfaces. The inside surfaces are velvety. This variety holds its color well, even in the hottest weather.

The petals are ovate in shape, with no distinct notching, of medium thickness, velvety on inner surface.

The veining of the petals is very delicate.

The flowers of this variety have long-lasting qualities, the cut flowers lasting a week or more. They are intensely fragrant, in fact the fragrance is more pronounced than in any other rose known to the inventor.

The nearest approach to this new variety is the Mrs. J. D. Eisele which has one parent in common (Premier Supreme) with the new variety. This new variety may be readily distinguished from the Mrs. J. D. Eisele by:

1. Its more perfect form, regular imbrication
2. Its more intense fragrance
3. Its much lighter and more uniform coloring
4. Its pointed rather than rounded leaves
5. Its larger bush growth Having thus disclosed my invention, what I claim as new is:

The variety of hybrid tea rose herein shown and described, characterized particularly by its ultra-vigorous growth, its blossoms of rich "rose red" to "rose color", perfect form, and intense fragrance, together with its desirable bedding qualities.

In testimony whereof I affix my signature.

FREDERICK HUBER HOWARD.